United States Patent
Assaker et al.

(10) Patent No.: US 11,864,800 B2
(45) Date of Patent: Jan. 9, 2024

(54) TRIANGULATION ASSEMBLY FOR RECTIFYING VERTEBRAE, AND SPINAL OSTEOSYNTHESIS SYSTEM COMPRISING SUCH ASSEMBLIES

(71) Applicant: STRYKER EUROPEAN OPERATIONS LIMITED, Cork (IE)

(72) Inventors: Richard Assaker, Kain (BE); Daniel Chopin, Mercurey (FR); Dominique Petit, Verton (FR)

(73) Assignee: STRYKER EUROPEAN OPERATIONS LIMITED, Cork (IE)

( * ) Notice: Subject to any disclaimer, the term of this patent is extended or adjusted under 35 U.S.C. 154(b) by 577 days.

(21) Appl. No.: 17/046,676

(22) PCT Filed: Apr. 12, 2019

(86) PCT No.: PCT/FR2019/050866
§ 371 (c)(1),
(2) Date: Mar. 1, 2021

(87) PCT Pub. No.: WO2019/197787
PCT Pub. Date: Oct. 17, 2019

(65) Prior Publication Data
US 2021/0212732 A1    Jul. 15, 2021

(30) Foreign Application Priority Data
Apr. 12, 2018    (FR) .................................. 1853204

(51) Int. Cl.
*A61B 17/70*    (2006.01)

(52) U.S. Cl.
CPC ...... *A61B 17/7041* (2013.01); *A61B 17/7013* (2013.01)

(58) Field of Classification Search
CPC ............ A61B 17/7001; A61B 17/7013; A61B 17/7041; A61B 17/7049
(Continued)

(56) References Cited

U.S. PATENT DOCUMENTS 5,425,732 A * 6/1995 Ulrich ................ A61B 17/7014
606/328
6,749,613 B1    6/2004 Conchy et al.
(Continued)

OTHER PUBLICATIONS

International Search Report for International Application No. PCT/FR2019/050866 dated Jul. 25, 2019, 3 pages.
(Continued)

*Primary Examiner* — Eduardo C Robert
*Assistant Examiner* — Christina Negrellirodriguez
(74) *Attorney, Agent, or Firm* — Duane Morris LLP (57) ABSTRACT

An assembly for rectifying vertebrae, comprises: two bone anchoring means intended to be implanted on a same vertebra, a triangulation bar and a connection means for connecting the triangulation bar to each bone anchoring means and for holding the bone anchoring means in a given position in order to form, with the triangulation bar connected to the bone anchoring means by means of the connection means, a rigid triangular assembly, the triangulation bar comprising an attachment area for attaching a correction instrument arranged to ensure a rigid attachment in rotation and in translation of the correction instrument on the triangulation bar.

19 Claims, 11 Drawing Sheets

(58) Field of Classification Search
USPC .................................... 606/250, 260, 278
See application file for complete search history.

(56) References Cited

U.S. PATENT DOCUMENTS

| | | |
|---|---|---|
| 7,794,464 B2 | 9/2010 | Bridwell et al. |
| 9,198,696 B1 * | 12/2015 | Bannigan ............ A61B 17/7052 |
| 9,211,145 B2 | 12/2015 | Pereiro de Lamo et al. |
| 2010/0211100 A1 | 8/2010 | Mack |

OTHER PUBLICATIONS

International Written Opinion for International Application No. PCT/FR2019/050866 dated Jul. 25, 2019, 6 pages.

* cited by examiner

TRIANGULATION ASSEMBLY FOR RECTIFYING VERTEBRAE, AND SPINAL OSTEOSYNTHESIS SYSTEM COMPRISING SUCH ASSEMBLIES

CROSS-REFERENCE TO RELATED APPLICATIONS

This application is a national phase entry under 35 U.S.C. § 371 of International Patent Application PCT/FR2019/050866, filed Apr. 12, 2019, designating the United States of America and published as International Patent Publication WO 2019/197787 A1 on Oct. 17, 2019, which claims the benefit under Article 8 of the Patent Cooperation Treaty to French Patent Application Serial No. 1853204, filed Apr. 12, 2018.

TECHNICAL FIELD

The present disclosure relates to an assembly enabling the rectification of vertebrae, and, in particular, but not exclusively, of lumbar vertebrae via the posterior approach, and a system for spinal osteosynthesis comprising such assemblies.

BACKGROUND

Lumbar vertebrae are conventionally rectified using systems for spinal osteosynthesis comprising bone anchoring means of the pedicle screw type, implanted in successive vertebrae involved in the rectification, and connected longitudinally to one another by connecting rods or plates via connection means.

However, the rectification of vertebrae using existing lumbar spinal osteosynthesis systems encounters several problems, associated, in particular, with the bending and placing of the connecting rods.

Indeed, in the case of monoaxial pedicle screws, it is necessary to adapt the connecting rods with suitable curvatures. However, the bending of the connecting rods is not an easy or precise operation to perform, and becomes increasingly difficult, the more pronounced the deformation of the vertebral column is. In addition, the correction is effectively limited by the curvature given to the connecting rod in combination with the angle at which the screws are inserted into the pedicles. Moreover, in the event of a significant correction, the corrective forces directly applied to the pedicle screws may adversely affect the quality of the anchorage, and, in particular, in the case of osteoporotic bones, may cause the pedicle screws to be torn out.

In order to overcome these disadvantages of monoaxial pedicle screws, it is known to replace monoaxial screws with multiaxial pedicle screws. However, the use of multiaxial screws does not prove entirely satisfactory, since they require the vertebrae to be reduced either by the technique of patient positioning, or by techniques of bending the connecting rod, which techniques are however relatively heavy-handed, long and complicated and do not systematically ensure, like monoaxial pedicle screws, the proper rectification of the vertebrae. In addition, the use of multi-axial screws results in a loss of correction.

Thus, whether the pedicle screws used are monoaxial or multiaxial screws, it proves particularly difficult to achieve a precise correction in 3 dimensions (sagittal, coronal and transverse). Additionally, it is not possible to systematically ensure proper rectification of the vertebrae.

The present disclosure aims to solve these problems by proposing a rectification assembly, and also a system for spinal osteosynthesis comprising such assemblies, enabling precise sagittal, coronal and transverse corrections with a large capacity for these corrections, while ensuring a satisfactory quality of attachment to the vertebrae.

BRIEF SUMMARY

To this end, and according to a first aspect, the present disclosure relates to an assembly for rectifying vertebrae, comprising two bone anchoring means intended to be implanted on a same vertebra, a structure for bridging the bone anchoring means to one another, the bridging structure, which is implantable, comprising a triangulation bar and connection means for connecting the triangulation bar to each bone anchoring means, a correction instrument mounted on the triangulation bar, means for locking the triangulation bar on the bone anchoring means via the connection means, the triangulation bar thus forming, with the bone anchoring means, a rigid triangular assembly, and means for adjusting the angular position of the correction instrument relative to the vertebra at a determined angle.

The implanted triangulation bar, associated with the convergent position of the bone anchoring means inherent to the very constitution of the vertebra, makes it possible to obtain a rigid triangular attachment assembly, which is reinforced and inseparable from the vertebrae. This thus makes it possible to perform corrective maneuvers in 3 dimensions, directly applied to the vertebra on which the assembly is mounted, and without a risk of damaging the bone anchorages. Moreover, the possibility of adjusting the angular position of the correction instrument relative to the vertebra on which it is mounted will enable the surgeon to establish a reference point, making it possible to simply and easily achieve the desired rectification of the vertebra.

According to a first configuration of an embodiment of the present disclosure, the connection means comprise means for adjusting the angular position of the correction instrument.

Advantageously, the triangulation bar comprises an attachment area for the correction instrument, arranged to provide secure attachment, in rotation and in translation, of the correction instrument on the triangulation bar.

Advantageously, the triangulation bar comprises a flattened portion forming the attachment area.

According to another configuration of an embodiment the present disclosure, the means for adjusting the angular position of the correction instrument are fitted on the triangulation bar.

Advantageously, the triangulation bar comprises an attachment area for the correction instrument, arranged to permit at least one displacement of the correction instrument on the triangulation bar in the sagittal plane, the attachment area forming the means for adjusting the angular position of the correction instrument. According to a particular embodiment, the triangulation bar comprises a notched part forming the attachment area.

Advantageously, the attachment area is central.

Advantageously, the connection means comprise two connectors each comprising a first passage area defining a longitudinal passage axis for the triangulation bar and a second passage area arranged to receive one of the bone anchoring means, the second passage area having an oblong form oriented parallel to the longitudinal passage axis of the first passage area, the connectors forming the means for adjusting the angular position of the correction instrument.

Advantageously, the second passage area is offset relative to the longitudinal passage axis.

Advantageously, the first passage area is shaped to enable the sliding and the rotation of the triangulation bar within itself before it is locked on the bone anchoring means. After the triangulation bar is locked on the two bone anchoring means, the latter form, with the triangulation bar, a rigid triangular attachment assembly with no degrees of freedom.

According to a particular configuration, each connector is in the form of a clip comprising a part having a C-shaped section extended by two arms comprising, respectively, an orifice, the orifices of each arm being arranged facing one another so as to define the second passage area, while the C-shaped section delimits the first passage area. It may advantageously be provided that the arm orifices are arranged to have an axial offset relative to one another. This arrangement makes it possible to obtain greater clamping on the rod, due to the shearing effect.

Advantageously, each bone anchoring means comprises a fixed screw head extended on either side by a lower threaded part for implantation in the vertebra and an upper threaded part onto which a retaining nut, forming the locking means, is intended to be screwed.

Advantageously, the triangulation bar is straight or curved.

The present disclosure also relates to a connector intended to be implemented with a rectification assembly such as, for example, as described above, the connector being arranged to enable the adjustment of the angular position of a correction instrument. The connector has all the characteristics described above. In particular, it comprises a first passage area defining a longitudinal passage axis for a triangulation bar and a second passage area arranged to receive a bone anchoring means, which second passage area has an oblong form oriented parallel to the longitudinal passage axis of the first passage area. According to a particular configuration, the connector is in the form of a clip comprising a part having a C-shaped section extended by two arms comprising, respectively, an orifice, the orifices of each arm being arranged facing one another so as to define the second passage area, while the C-shaped section delimits the first passage area. It may advantageously be provided that the arm orifices are arranged to have an axial offset relative to one another. This arrangement makes it possible to obtain greater clamping on the rod, due to the shearing effect.

The present disclosure also relates to a system for spinal osteosynthesis comprising at least two assemblies for rectifying vertebrae as described above, the assemblies being intended to be implanted on two discrete vertebrae and to be connected to one another.

Advantageously, the system comprises at least one maneuvering instrument connecting the correction instruments of each of the triangulation assemblies to one another.

The present disclosure also relates to a method for rectifying vertebrae using two assemblies for rectifying vertebrae as described above and comprising the following steps:
implanting first bone anchoring means in a first vertebra,
implanting second bone anchoring means in a second vertebra
connecting the first bone anchoring means to one another by means of a first triangulation bar comprising first means for attaching a first correction instrument, the first triangulation bar forming a first implanted bridging structure,
connecting the second bone anchoring means to one another by means of a second triangulation bar comprising second means for attaching a second correction instrument, the second triangulation bar forming a second implanted bridging structure,
positioning the first and second correction instruments relative to one another at an angle corresponding to the desired sagittal angular correction and locking the first and second correction instruments in position,
and, after locking the first and second correction instruments in position, displacing the first and/or the second correction instrument in order to position them parallel to one another.

According to a first embodiment, the positioning of the first and second correction instruments at an angle corresponding to the desired sagittal angular correction is carried out by pivoting the first and second triangulation bars on the first and second bone anchoring means. The adjustment of the angular position of the correction instruments is made possible by implementing means for connecting the triangulation bars to the bone anchoring means, which connection means are arranged to permit, before locking, a multi-axial movement of the triangulation bars on the bone anchoring means. The locking of the first and second correction instruments in position is then carried out by locking the triangulation bars on the first and second bone anchoring means.

According to another embodiment, the positioning of the first and second correction instruments at an angle corresponding to the desired sagittal angular correction is carried out by pivoting the correction instruments on their respective triangulation bars via the attachment means of the bars, arranged to enable such a pivoting movement.

The placing of the triangulation bars and the positioning of the correction instruments at a defined angle before locking enables optimal and precise control of the sagittal, coronal and transverse corrections.

Advantageously, the first and second correction instruments are attached, respectively, to the first and second triangulation bar, at the first and second attachment means, prior to the triangulation bars being placed on the associated bone anchoring means.

BRIEF DESCRIPTION OF THE DRAWINGS

Other subjects and advantages of the present disclosure will become apparent from the following description, made with reference to the appended drawings, in which:

FIGS. 12 to 18b show the steps of placing two rectification assemblies with a view to rectifying vertebrae;

DETAILED DESCRIPTION

In relation to FIGS. 1 to 11, an embodiment of an assembly 1 for rectifying vertebrae according to the present disclosure is described.

Figure 1:
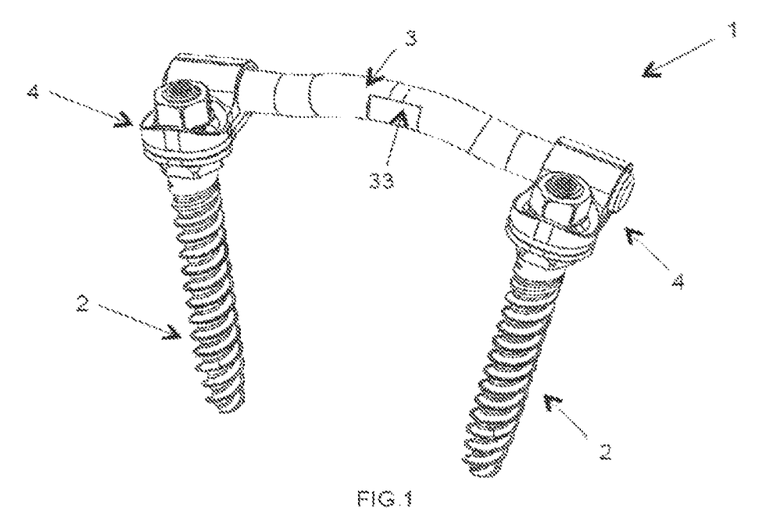
FIG. 1 shows a schematic view of an assembly for rectifying vertebrae according to one embodiment.
Figure 2:
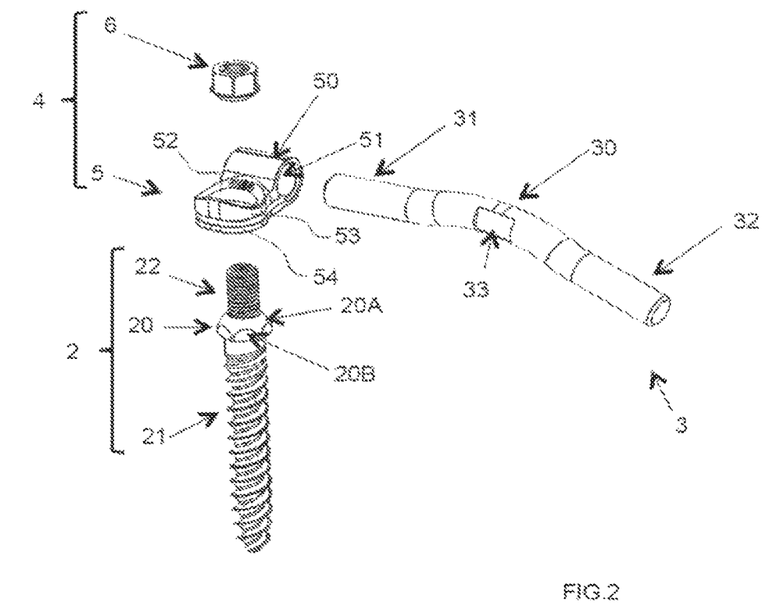
FIG. 2 shows a partial exploded view of the assembly for rectifying vertebrae of FIG. 1.

The rectification assembly 1 comprises two bone anchoring means 2 intended to be implanted on a same vertebra 100, a triangulation bar 3 and connection means 4 for connecting the triangulation bar to each bone anchoring means.

Figures 3, 4:
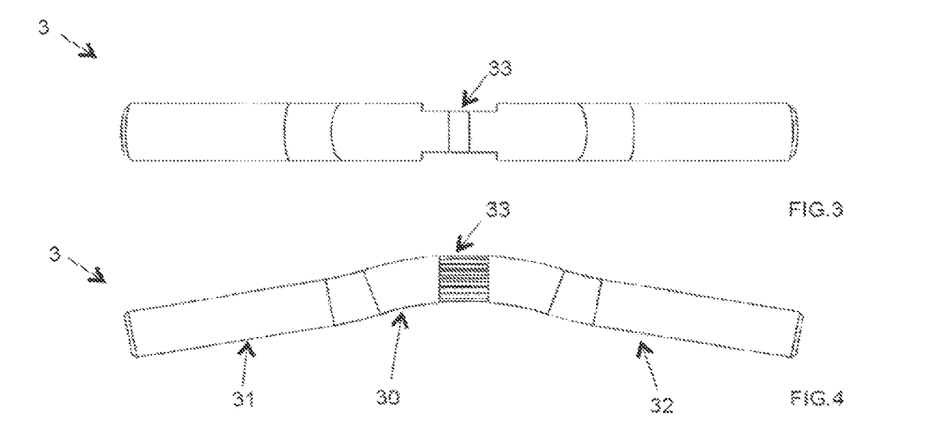
FIG. 3 shows a plan view of the triangulation bar implemented in the assembly for rectifying vertebrae of FIG. 1.
FIG. 4 shows another embodiment of the triangulation bar.

In the embodiment illustrated, the triangulation bar 3 (of circular section in the example) is advantageously omega-shaped in order to follow the form of the vertebra 100 on which it is mounted. More particularly, it comprises a central part 30 and two end parts 31, 32, which are, respectively, linear, the end parts each being connected to the central part by a curved portion.

In order to rectify the vertebrae according to the technique described below, the triangulation bar 3 comprises an attachment area 33 enabling the attachment of a correction instrument 10. In the embodiment illustrated, the attachment area 33 is provided at the central part 30. It is formed of two flattened portions arranged on either side of the bar. They are arranged centrally in the curved part.

The connection means 4 associated with each anchoring means 2 comprise a connector 5 and a retaining nut 6.

Figure 5:
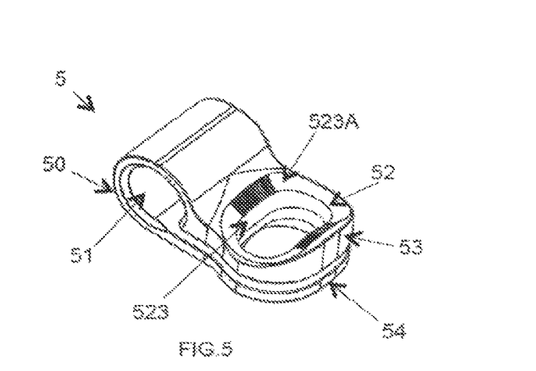
FIGS. 5 to 7 show, respectively, perspective, plan and side views of the connector implemented in the assembly for rectifying vertebrae of FIG. 1.
Figure 6:
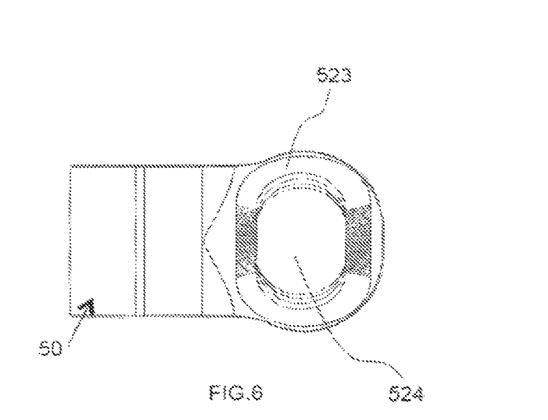
Figure 7:
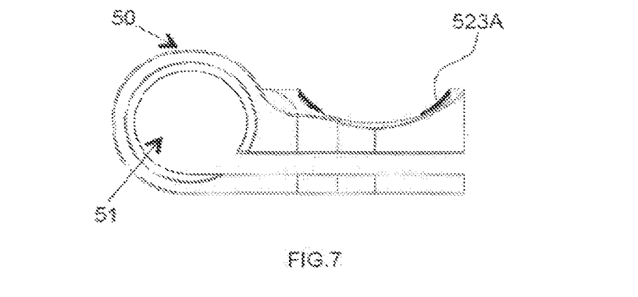
Figure 8:
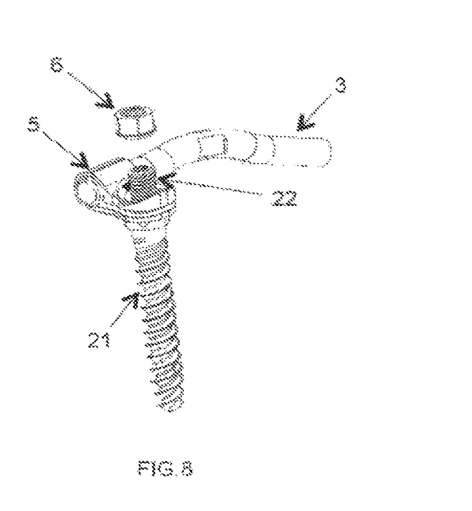
FIGS. 8 and 9 show a perspective detail view of the rectification assembly, before and after, respectively, placing the retaining nut.
Figure 9:
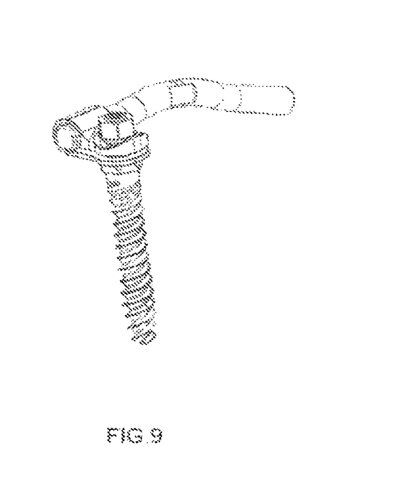
Figure 10:
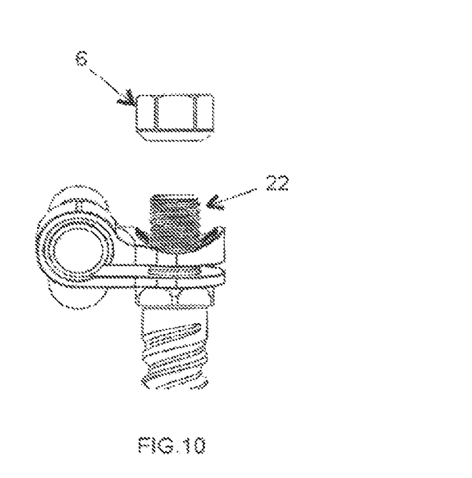
FIGS. 10 and 11 show a lateral view of the rectification assembly illustrated in FIGS. 8 and 10.
Figure 11:
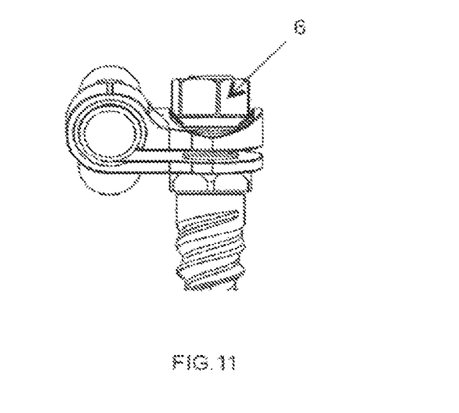

Each connector 5 comprises a first and a second passage area 51, 52, the first area being arranged to receive the end parts 31, 32 of the triangulation bar 3, the second area being arranged to receive one of the bone anchoring means 2. Advantageously, the second passage area 52 is offset relative to the first passage area 51 and defines a longitudinal passage axis perpendicular to the longitudinal passage axis of the first passage area 51.

According to an advantageous configuration, the second passage area 52 is advantageously of oblong form in order to enable the attachment of the rectification assembly in a configuration in which the triangulation bar 3 and the anchoring means 2 are not perpendicular. In the embodiment described, the angular displacement is +/−15°. Advantageously, the second passage area 52 is arranged in order to enable a rotation of the connector 5 on the anchoring means 2 and thus to enable the adaptability of the triangulation bar when the latter is not perpendicular to the anchoring means 2.

In the embodiment illustrated, each connector 5 is in the form of a clip, generally U-shaped, comprising two arms 53, 54 extending facing one another at a distance from one another and, at the starting point of the arms 53, 54, a tubular portion 50 having a C-shaped section defining the first passage area 51 for receiving the triangulation bar 3. Each arm 53, 54 of the connector comprises a through-orifice 523, 524 defining the second passage area 52. Advantageously, the through-orifices 523, 524, respectively, have an oblong form oriented parallel to the longitudinal passage axis of the first passage area 51, the through-orifice 523 having a length greater than that of the through-orifice 524. This arrangement of the orifices 523, 524 of oblong form has the advantage of enabling the free rotation of the connector 5 on the bone anchoring means before locking thereof. As illustrated in the figures, the second passage area 52 is offset from the longitudinal passage axis.

In the embodiment illustrated, the through-orifices 523, 524 are arranged coaxially, facing one another. According to a variant embodiment, the through-orifices 523, 524 may be arranged to have a slight offset relative to one another in order to ensure a greater clamping pressure on the rod due to the shearing effect.

Advantageously, the through-orifice 523 of the upper arm (arm 53) is delimited by an inner bearing surface 523A having a curved form shaped to receive one of the retaining nuts 6, the retaining nuts 6 each having a base of convex form able to cooperate with the inner bearing surface of the through-orifice 523 of the arm 53.

Advantageously, the first passage area 51 is shaped to enable the sliding and the rotation of the triangulation bar 3 within itself before it is locked on the connectors 5 via the retaining nuts 6.

The connectors, which have just been described are thus arranged to form adjustment means, which will make it possible to adjust the angular position of a correction instrument mounted on the triangulation bar 3, as will be described below. It may also be provided that the adjustment means are borne not by the connectors but by the triangulation bar 3. FIG. 4 gives an example of a triangulation bar 3 in which the attachment area 33 comprises a notch. It is thus possible to adjust the angular position of the correction instrument.

In the embodiment illustrated, the bone anchoring means 2 are in the form of a pan-head anchoring screw. Hereinafter, no distinction will be made between "bone anchoring means" and "anchoring screws."

Each anchoring screw 2 comprises a screw head 20 extended on either side by threaded parts 21, 22, the lower threaded part 21 being shaped for implantation in the vertebra, the upper threaded part 22 being shaped to receive one of the retaining nuts 6. Moreover, the screw head 20 comprises a convex spherical upper face 20A and, in the lower part, a lateral face 20B having a 6-sided imprint. As will be seen below, the connector 5 is positioned on the associated anchoring screw 2, the lower face of the lower arm 54, advantageously of complementary form, bearing against the spherical upper face 20A of spherical form of the screw head 20, the latter serving as pivot during the rectification of the vertebrae. The retaining nut 6, under the application of a tightening torque, causes the arms 53, 54 to come closer to one another, until the triangulation bar 3 is locked in the connection means 4 (FIGS. 8 to 11).

FIGS. 12 to 19b illustrate the placing of two rectification assemblies 1 as described above and the implementation thereof for rectifying vertebrae.

Figure 12:
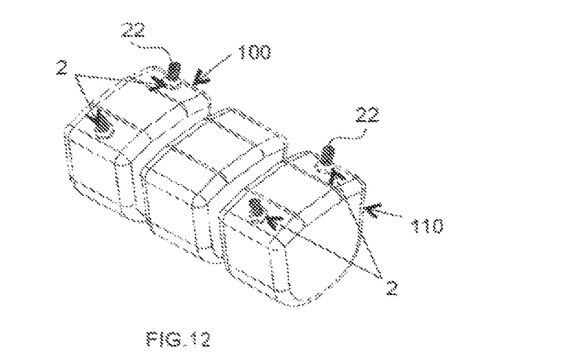

Firstly, the anchoring screws 2 of each of the rectification assemblies are placed on the two vertebrae 100, 110 located on either side of the area of the spinal column to be treated (FIG. 12). Each anchoring screw 2 is implanted at one of the pedicles of the associated vertebra (the figures show simplified vertebrae). The anchoring screws 2 of each vertebra 100, 110 are implanted so as to each converge in the direction of the other.

Figure 13A:
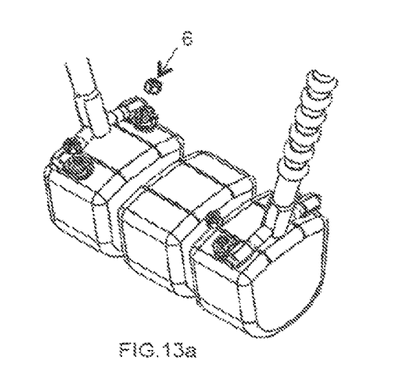
Figure 13B:
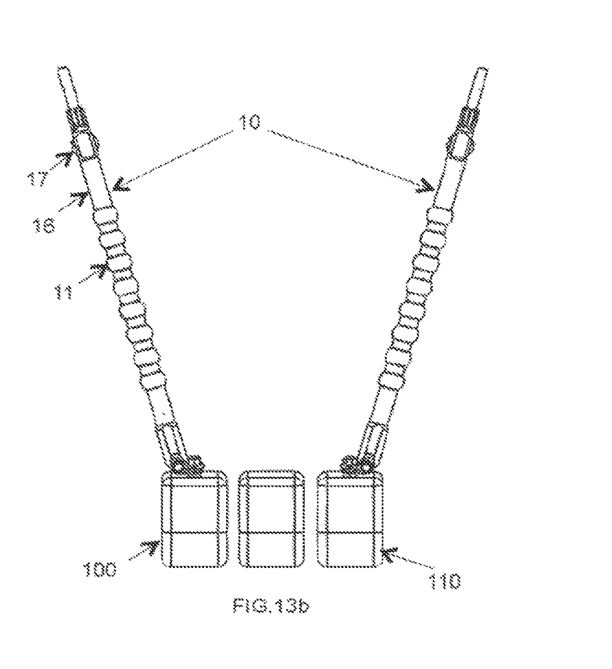

The anchoring screws 2 of the same vertebra are then connected to one another with a triangulation bar 3 by threading, through the second passage 52 of each connector 5 fitted to the ends of the bar, the upper threaded part 22 of the anchoring screw 2 in question until the lower arm 54 of the connector 5 comes to bear against the spherical upper face 20A of the screw head 20. This step is carried out using a handling instrument 10 attached beforehand to the attachment area of the triangulation bar 3 (FIGS. 13a and 13b). In the embodiment illustrated, the handling instrument 10 is intended to also ensure the correction of the vertebrae. Hereinafter, it will be referred to as correction instrument 10. In the embodiment illustrated, the correction instrument 10 is formed of a shaft 16 provided with a plurality of attachment means 11 intended to enable the attachment of additional instruments, and, in particular, "maneuvering" instruments. Advantageously, the attachment means 11 form a ball joint in order to enable multi-directional connection to the additional instruments, the ball joint being lockable at any time. The correction instrument 10 comprises, at the end opposite to the end for attachment to the triangulation bar 3, a handle 17. Advantageously, the handle 17 is arranged to have extensions 18 extending on either side of the shaft, and advantageously perpendicular thereto, in the transverse plane of the vertebrae when the correction instrument 10 is mounted thereon.

Figure 13C:
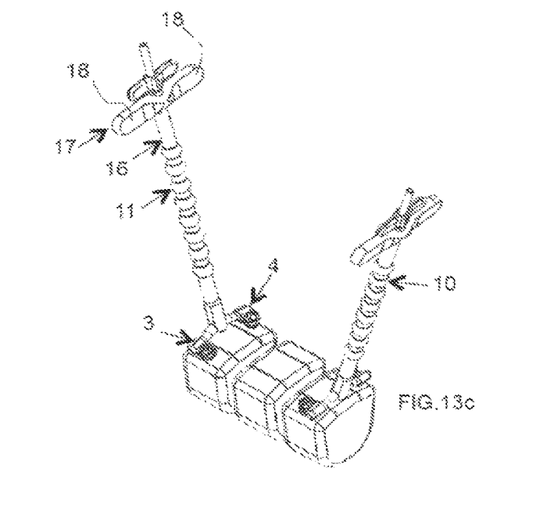

The retaining nuts 6 are then placed on the upper threaded part 22 of the screw head 20 emerging from the connector 5 without however being completely screwed on, so as not to block either the displacement of the triangulation bar 3 through the connector 5 or the movement of the connectors 5 on the anchoring screws 2 (FIG. 13c).

The correction instruments 10 are then positioned at an angle α relative to one another, which angle corresponds to the sagittal angular correction determined beforehand by the surgeon, which is generally chosen to obtain optimum sagittal balance of the patient using an angle-measuring instrument 15. In the case of an osteotomy, the angular position of the correction instruments 10 is chosen to correspond to the ultimately desired lordosis angle.

Once the angle between the correction instruments 10 has been reached, the nuts 6 are finally tightened to hold the triangular attachment assemblies in a fixed and rigid position on each of the vertebrae.

Maneuvering instruments 12, 13, connecting the correction instruments 10 of each of the triangulation assemblies, are then put in place on the attachment means 11 of the correction instruments 10. The maneuvering instruments comprise a rack and pinion system enabling the correction instruments 10 to be gradually moved away from, or closer to, one another via the triangulation assemblies, and therefore enabling gradual compression or distraction of the vertebrae relative to one another. The fixed and rigid position of the attachment assembly obtained using the maneuvering instruments makes it possible to stabilize the vertebrae in any position, and thereby to perform a number of surgical gestures on a stable spinal column. In the case of an osteotomy, this fixed and rigid position provides essential stability to the surgical gesture, since the partial ablation of a vertebra results in significant instability of the spinal column.

Figure 14A:
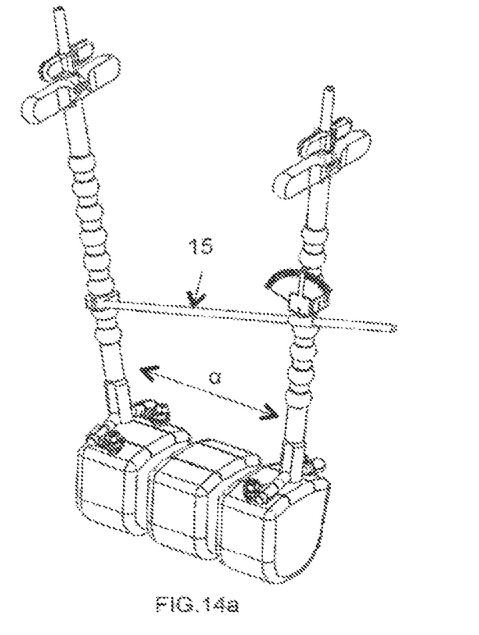
Figure 14B:
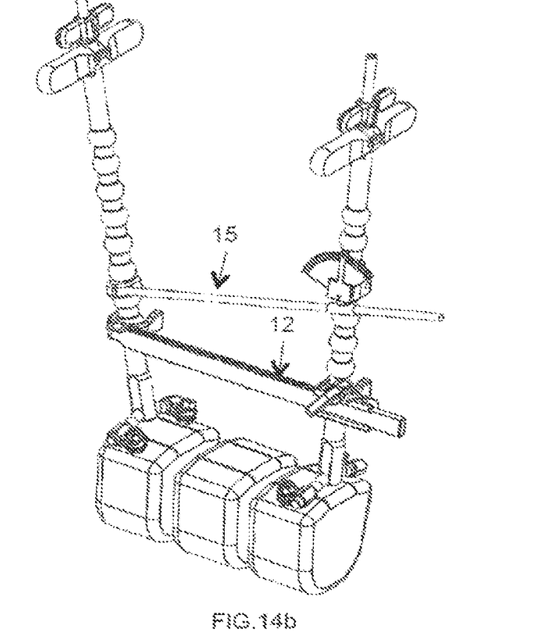
Figure 15A:
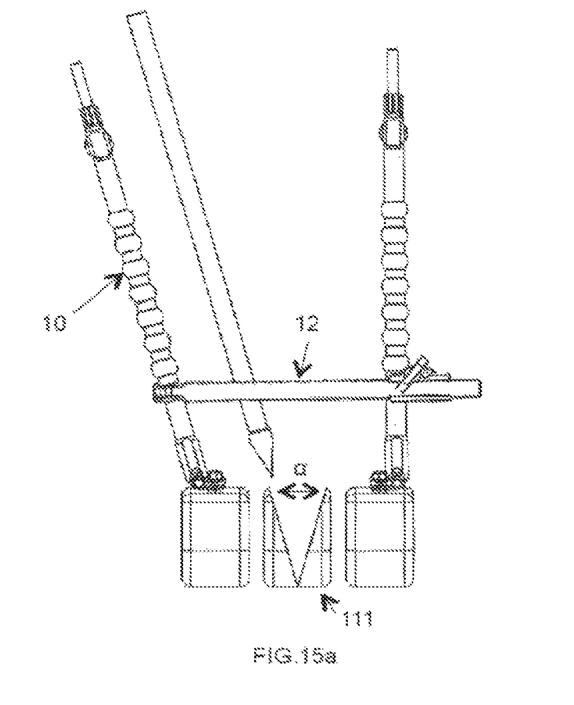
Figure 15B:
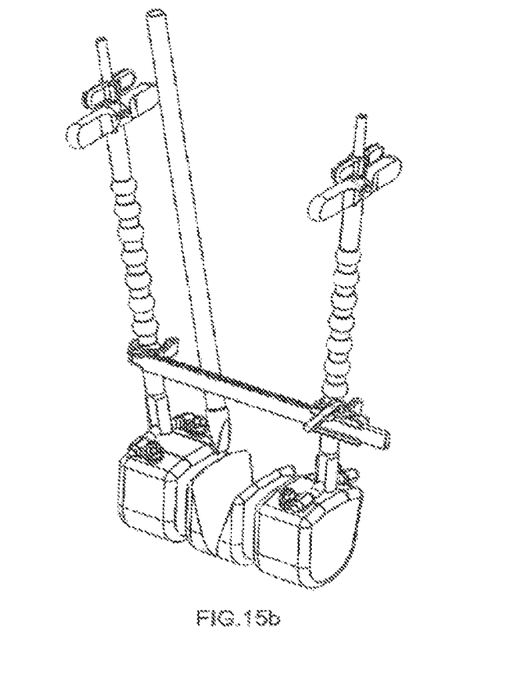

A first maneuvering instrument 12, connecting the correction instruments 10 of each of the rectification assemblies, is thus put in place (FIGS. 14a and 14b). This first instrument enables, aside from the compression/distraction of the vertebra 100, 110 carried out subsequently, an angular correction of the vertebrae. The anteroposterior displacement of this maneuvering instrument also enables direct anteroposterior positional correction of the vertebrae, advantageously in the case of spondylolisthesis. This displacement/correction is possible by the combination of the correction instruments 10, maneuvering instrument positioned in the form of a frame and the attachment means between these instruments, of ball joint type. A handle, not shown here, could also be positioned at the end of the maneuvering instrument in order to facilitate this displacement. Another advantage of this first instrument is that of avoiding any instability of the spine when the ball joints are locked.

When an osteotomy is necessary, the vertebral bone is cut in a V shape (FIGS. 15a and 15b) with an angle corresponding to the ultimately desired lordosis angle and thus corresponding to the angular distance of the correction instruments 10 relative to one another (spacing at angle α). To this end, the angular positioning of the correction instruments 10 in the predefined position forms a guide for the osteotomy bone-cutting instruments, with the vertebral bone cuts in a V shape being made parallel to the correction instruments 10.

Figure 16:
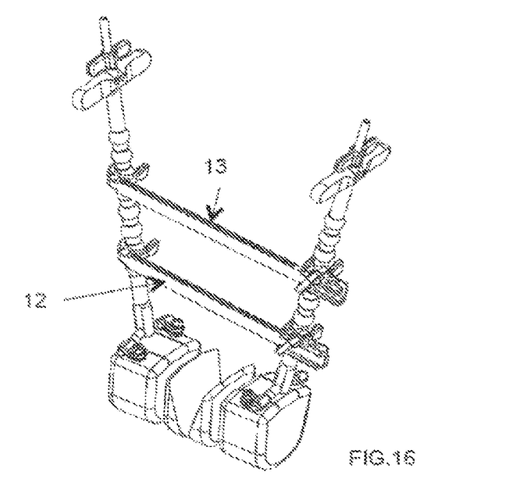

In order to control the compression/distraction correction of the vertebrae with instruments between them, a second maneuvering instrument 13 can be placed between the two correction instruments 10 (FIG. 16).

Once the maneuvering instruments are in place, the correction of the vertebrae is performed. For this purpose, the correction instruments 10 are acted upon until they are placed parallel to one another (FIGS. 17a and 17b), the final parallel positioning of the correction instruments 10 corresponding to the optimal correction of the sagittal angle, the two faces of the V shape, created by the osteotomy, which may have been carried out, then being parallel or even colinear.

Figure 18A:
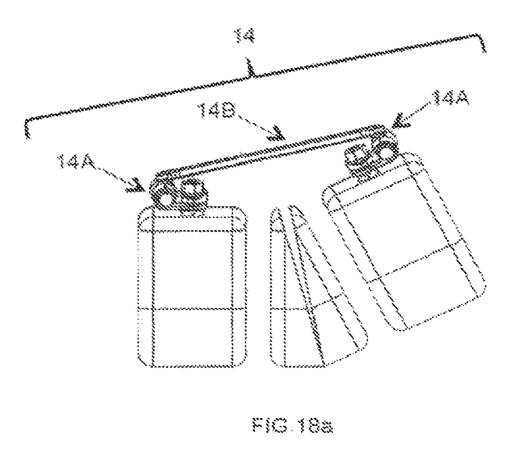
Figure 18B:
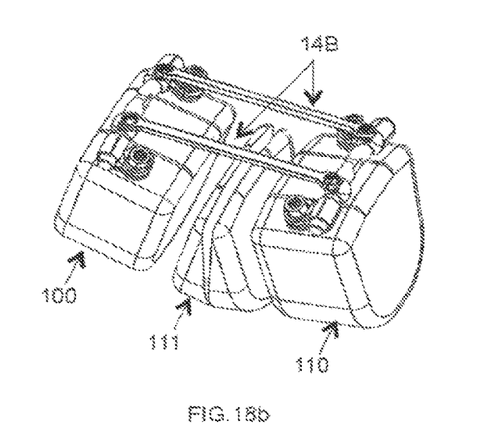

Once the correction has been carried out, it only remains to connect the triangular attachment assemblies together in order to fix the position thereof, before the correction instruments 10 are disassembled. This connecting can be carried out, for example, by means of a longitudinal attachment system 14 composed of hooks 14A and plates 14B (FIGS. 18a and 18b).

Figure 19A:
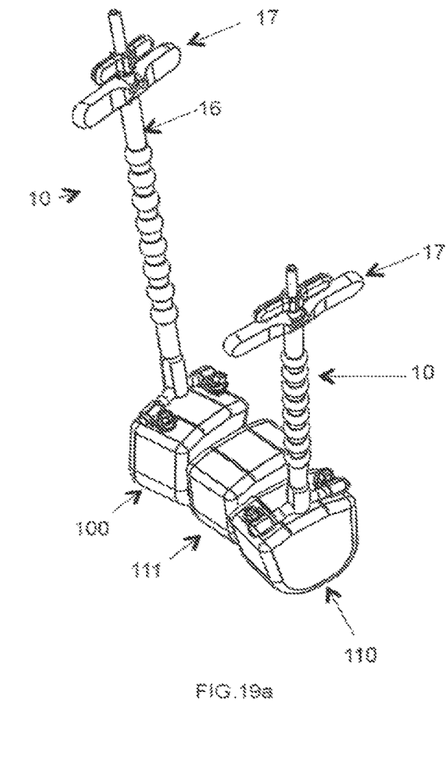
FIGS. 19a to 19c show, respectively, perspective, transverse and posterior views of vertebrae requiring rectification in 3 dimensions, the vertebrae being fitted with rectification assemblies according to the present disclosure.
Figure 19B:
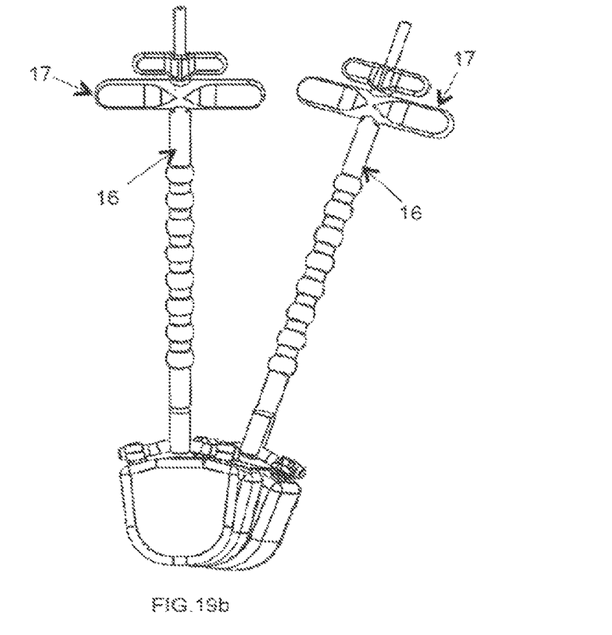
Figure 19C:
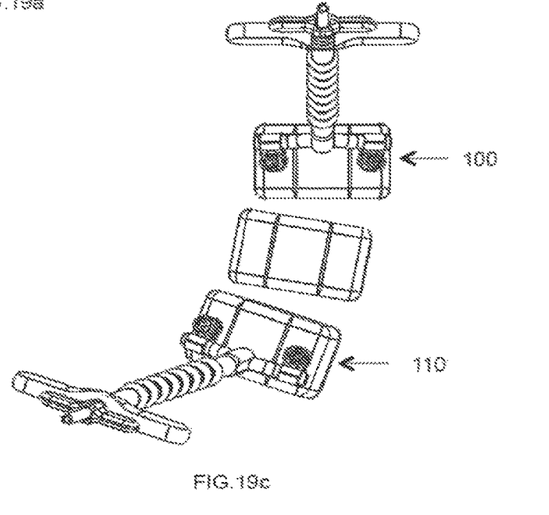

The preceding figures show vertebrae requiring rectification only in the sagittal plane. Of course, it is clear that the rectification system according to the present disclosure is not limited to this type of correction, the system being suitable for enabling corrections in 3 dimensions. FIGS. 19a to 19c show an example of vertebrae requiring such a correction. In order to facilitate understanding of the movement of the vertebrae performed during the rectification thereof using the rectification system according to the present disclosure, the maneuvering instruments are not shown.

Figure 17A:
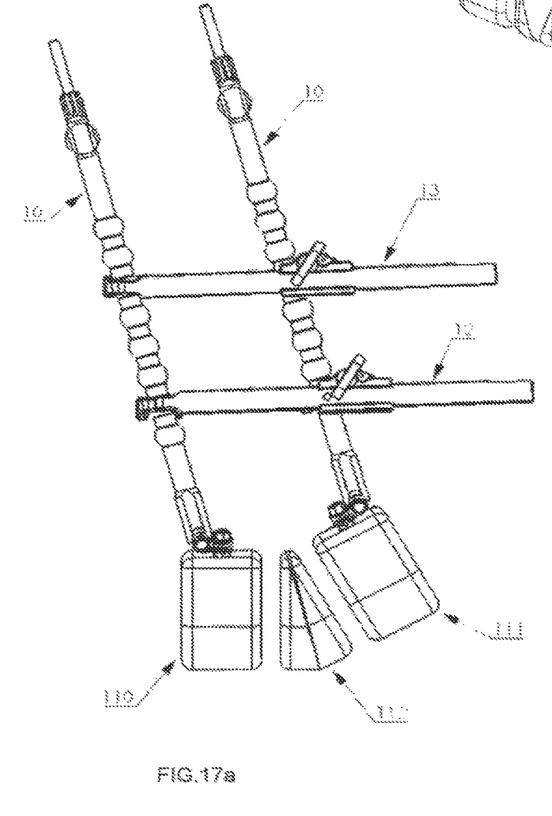
Figure 17B:
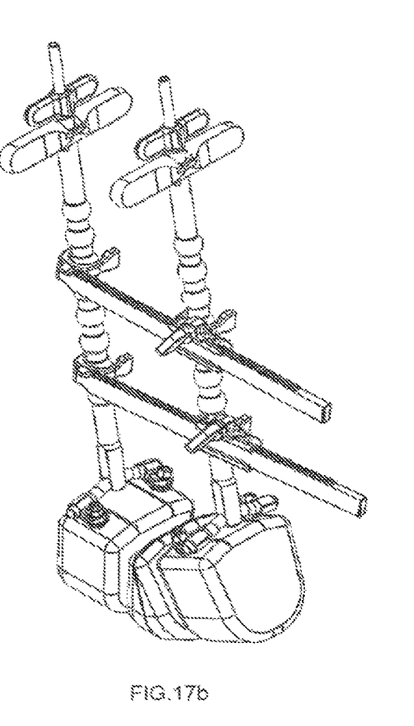
Figure 20A:
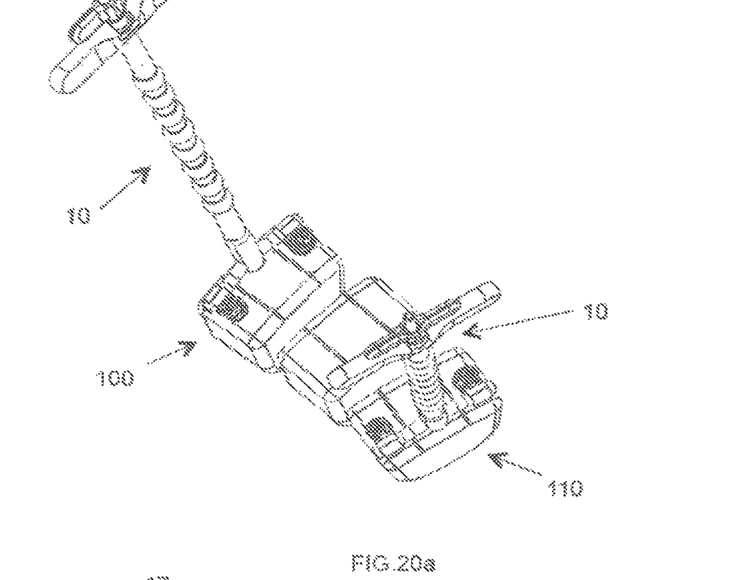
FIGS. 20a and 20b show the vertebrae illustrated in FIGS. 19a to 19c after a transverse rotation correction.
Figure 20B:
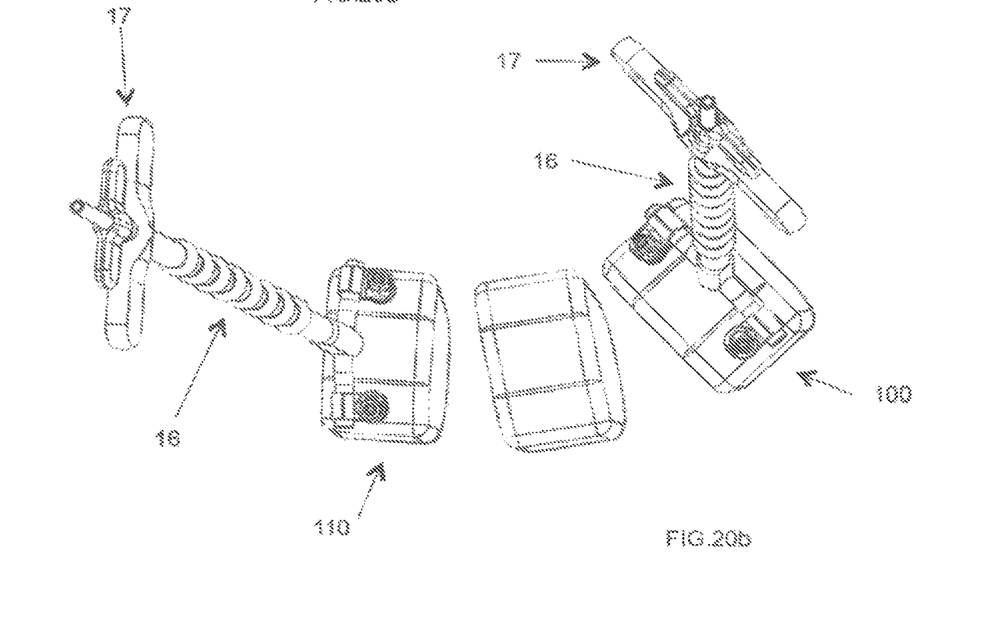
Figure 21A:
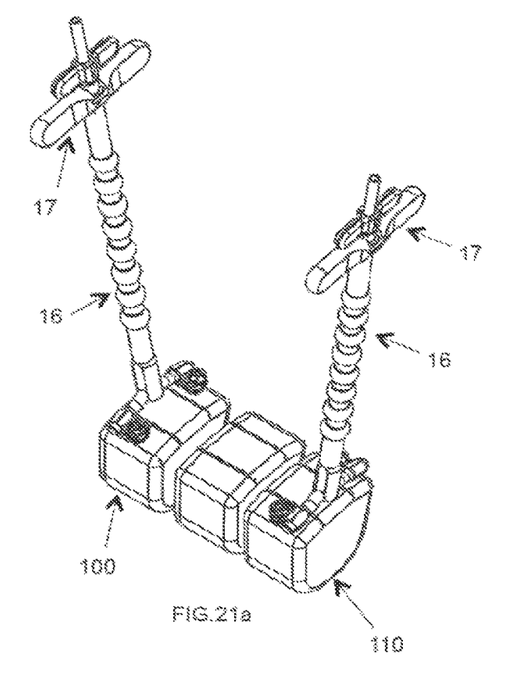
FIGS. 21a to 21c show the vertebrae illustrated in FIGS. 20a and 20b after a coronal shift correction.
Figure 21B:
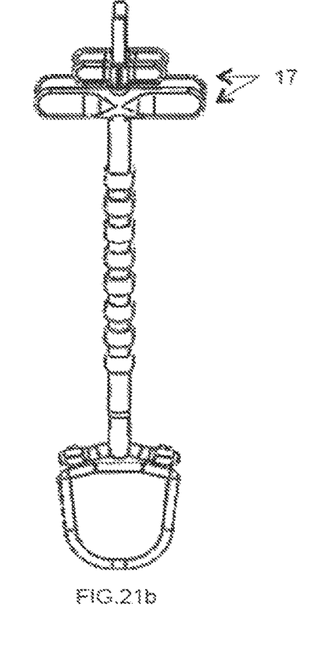
Figure 21C:
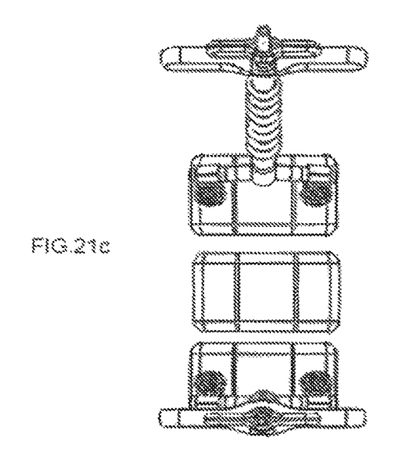

Thus, after having positioned the correction instruments 10 of each rectification assembly relative to one another at the sagittal angle α corresponding to the targeted posterolateral angular correction, a transverse rotation correction is carried out so as to bring the shafts 16 of the correction instruments 10 into the same plane, as illustrated in FIGS. 20a and 20b. A coronal shift correction is then carried out by positioning the handles 17 of the correction instruments 10 parallel with one another, as illustrated in FIGS. 21 to 21c. The sagittal correction of the vertebrae is then carried out, by bringing, as in the previous example of vertebral rectification, the shafts 16 of the correction instruments 10 parallel with one another (FIG. 17a).

The movements (transverse rotation, coronal shift and sagittal shift) applied to the vertebrae have been described sequentially. Of course, it is clear that all of these movements can be carried out in a single gesture. The measuring instrument 15 described in the initial phase of angular positioning of the correction instruments can also be used during all the surgical steps described, in order to monitor and measure the progression of the correction.

Figure 22:
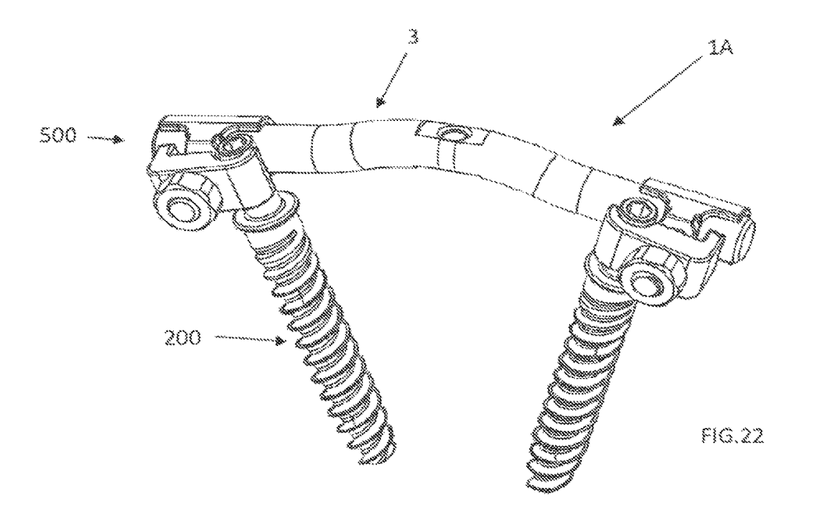
FIG. 22 shows a schematic view of an assembly for rectifying vertebrae according to another embodiment.
Figure 23:
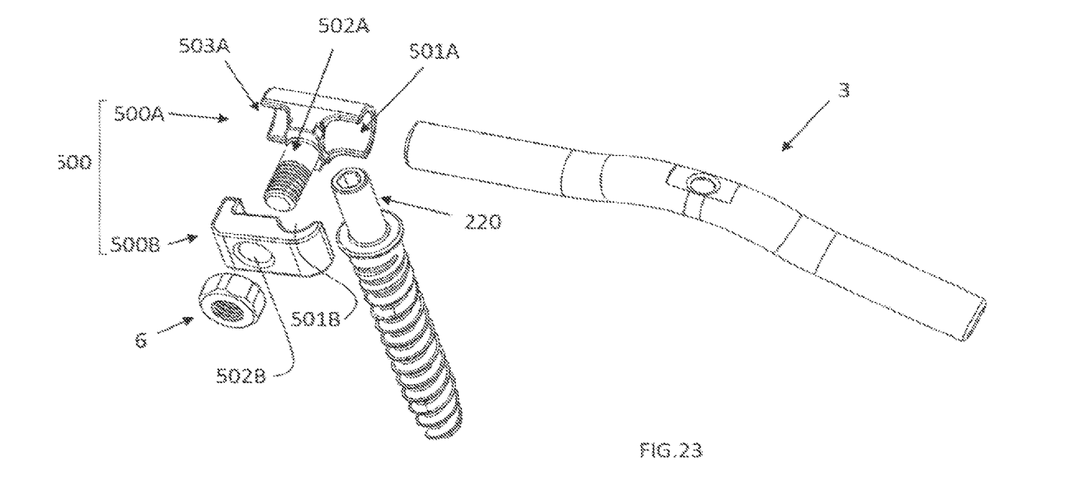
FIG. 23 shows a partial exploded view of the assembly for rectifying vertebrae of FIG. 22.

FIGS. 22 and 23 show a variant embodiment of an assembly for rectifying 1A vertebrae. The implementation of the assembly is similar to that described previously. However, the rectification assembly of this variant differs from that described previously in terms of the arrangement of the connectors 500 and also the bone anchoring means 200.

In this variant, the connector 500 is formed of two separate parts 500A, 500B.

One of the parts 500A forms a sleeve intended to receive the triangulation bar 3. The sleeve is provided at both of its ends with a notch 501A, 503A. It is provided on its outer face with a threaded shaft 502A. The notches are arranged facing one another on either side of the threaded shaft.

The other part 500B comprises a groove 501B arranged to receive the upper part 220 of the bone anchoring means. It comprises a hole 502B for the passage of the threaded shaft 502A. The groove 501B is arranged to be placed facing one of the notches 501A. Thus, when the two parts are assembled by tightening the retaining nut 6 on the threaded shaft 502A, which extends through the passage hole 502B, the upper part 220 of the bone anchoring means and the triangulation bar 3 are clamped by being pressed against one another, with the two parts acting as a vise.

As will be understood, the arrangement of sleeve/threaded rod/upper part of the bone anchoring means is such that it enables multiaxial movement of the triangulation bar before complete tightening of the nut, thereby enabling the adjustment of the angular position of the correction instrument mounted on the triangulation bar (instrument not shown).

Embodiments of the present disclosure are described above by way of example. Of course, a person skilled in the art is able to carry out different variant embodiments of the present disclosure without departing from the scope of the invention as defined by the claims.

The invention claimed is:

1. An assembly for rectifying vertebrae, comprising:
   two bone anchoring means intended to be implanted on a same vertebra;
   a structure for bridging the bone anchoring means to one another, the bridging structure, which is implantable, comprising a triangulation bar and connection means for connecting the triangulation bar to each bone anchoring means,
   a correction instrument mounted on the triangulation bar;
   means for locking the triangulation bar on the bone anchoring means via the connection means, the triangulation bar thus forming, with the bone anchoring means, a rigid triangular assembly, wherein the connection means comprise two connectors each comprising a first passage area defining a longitudinal passage axis for the triangulation bar and a second passage area arranged to receive one of the bone anchoring means, the second passage area having an oblong form oriented parallel to the longitudinal passage axis of the first passage area, the connectors forming the means for adjusting the angular position of the correction instrument; and
   means for adjusting an angular position of the correction instrument relative to the vertebra at a determined angle.

2. The assembly of claim 1, wherein the connection means comprises the means for adjusting the angular position of the correction instrument.

3. The assembly of claim 2, wherein the triangulation bar comprises an attachment area for the correction instrument, arranged to provide secure attachment, in rotation and in translation, of the correction instrument on the triangulation bar.

4. The assembly of claim 3, wherein the triangulation bar comprises a flattened portion forming the attachment area.

5. The assembly of claim 3, wherein the attachment area is central.

6. The assembly of claim 1, wherein the means for adjusting the angular position of the correction instrument are fitted on the triangulation bar.

7. The assembly of claim 6, wherein the triangulation bar comprises an attachment area for the correction instrument, arranged to permit at least one displacement of the correction instrument on the triangulation bar in a sagittal plane, the attachment area forming the means for adjusting the angular position of the correction instrument.

8. The assembly of claim 7, wherein the triangulation bar comprises a notched part forming the attachment area.

9. The assembly of claim 1, wherein the first passage area is shaped to enable a sliding and a rotation of the triangulation bar within itself before it is locked on the connectors.

10. The assembly of claim 1, wherein each connector is in the form of a clip comprising a part having a C-shaped section extended by two arms comprising, respectively, an orifice, the orifices of each arm being arranged facing one another to define the second passage area, while the C-shaped section delimits the first passage area.

11. The assembly of claim 10, wherein the orifices are arranged to have an axial offset relative to one another.

12. The assembly of claim 11, wherein each bone anchoring means comprises a fixed screw head extended on either side by a lower threaded part for implantation in the vertebra and an upper threaded part onto which a retaining nut, forming the means for locking the triangulation bar on the bone anchoring means, is intended to be screwed.

13. The assembly of claim 12, wherein the triangulation bar is straight or curved.

14. A system for spinal osteosynthesis comprising at least two assemblies for rectifying vertebrae according to claim 13, the assemblies being intended to be implanted on two discrete vertebrae and to be connected to one another.

15. The system of claim 14, further comprising at least one maneuvering instrument connecting the correction instruments of each of the triangulation assemblies to one another.

16. The assembly of claim 1, wherein the triangulation bar comprises an attachment area for the correction instrument, arranged to permit at least one displacement of the correction instrument on the triangulation bar in a sagittal plane, the attachment area forming the means for adjusting the angular position of the correction instrument.

17. The assembly of claim 1, wherein each bone anchoring means comprises a fixed screw head extended on either side by a lower threaded part for implantation in the vertebra and an upper threaded part onto which a retaining nut, forming the locking means, is intended to be screwed.

18. The assembly of claim 1, wherein the triangulation bar is straight or curved.

19. A system for spinal osteosynthesis comprising at least two assemblies for rectifying vertebrae according to claim 1, the assemblies being intended to be implanted on two discrete vertebrae and to be connected to one another.

* * * * *